(12) United States Patent
Warr et al.

(10) Patent No.: US 7,968,606 B2
(45) Date of Patent: Jun. 28, 2011

(54) PERFUME COMPOSITION HAVING SEDATIVE EFFECT

(75) Inventors: Jonathan Warr, Paris (FR); Satomi Kunieda, Hiratsuka (JP); Yoshiaki Numata, Hiratsuka (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 11/428,101

(22) Filed: Jun. 30, 2006

(65) Prior Publication Data

US 2006/0240055 A1    Oct. 26, 2006

Related U.S. Application Data

(62) Division of application No. 11/198,532, filed on Aug. 8, 2005, now abandoned.

(30) Foreign Application Priority Data

Aug. 6, 2004  (FR) ...................................... 04 08726

(51) Int. Cl.
*A01N 31/14*    (2006.01)
*A61K 31/075*    (2006.01)

(52) U.S. Cl. ...................................... 514/718

(58) Field of Classification Search .................... 424/400
See application file for complete search history.

(56) References Cited

U.S. PATENT DOCUMENTS

| 5,141,921 A | 8/1992 | Sawano et al. |
| 6,054,137 A * | 4/2000 | Breton et al. .................. 424/400 |
| 6,268,333 B1 | 7/2001 | Okazaki et al. |
| 2003/0084520 A1 | 5/2003 | Del Luca et al. |
| 2003/0133886 A1 | 7/2003 | Smith et al. |

FOREIGN PATENT DOCUMENTS

| JP | 05-125390 | 5/1993 |
| JP | 6-267729 A | 9/1994 |
| JP | 7-211533 A | 8/1995 |
| JP | 8-45725 A | 2/1996 |
| JP | 11-329822 A | 11/1999 |
| JP | 2000-86478 A | 3/2000 |
| JP | 2000-159523 A | 6/2000 |

OTHER PUBLICATIONS

Ya-Fei Ji, et al., "A High Yeild, Selective Synthesis of 1,3,5-Trimethoxybenzene", Organic Preparations and Procedures International, 2003, pp. 225-227, vol. 35, No. 2.

S. Kimura, et al., "Proceedings of the 19th Japanese Symposium on Taste and Smell", Sep. 9-11, 1985, pp. 65-68.

Harding, C.R. et al., "Dandruff: a condition characterized by decreased levels of intercellular lipids in scalp stratum corneum and impaired barrier function," Arch Dermatol Res, vol. 294, 2002, pp. 221-230.

* cited by examiner

*Primary Examiner* — Alton Pryor
(74) *Attorney, Agent, or Firm* — Sughrue Mion, PLLC

(57) ABSTRACT

The present invention provides a perfume composition, which comprises at least one trimethoxybenzene in an amount of less than 0.5% by weight based on the total weight of the perfume composition. The present invention also provides a method for providing sedation in a subject, which comprises applying a perfume composition comprising at least one trimethoxybenzene in an amount of less than 0.5% by weight based on the total weight of the perfume composition to the subject.

13 Claims, 2 Drawing Sheets

PERFUME COMPOSITION HAVING SEDATIVE EFFECT

This is a divisional of application Ser. No. 11/198,532 filed Aug. 8, 2005 now abandoned. The entire disclosure of the prior application, application Ser. No. 11/198,532, is considered part of the disclosure of the accompanying divisional application and is hereby incorporated by reference.

FIELD OF THE INVENTION

The present invention relates to a perfume composition having a sedative effect, and a method for providing sedation in a subject.

BACKGROUND OF THE INVENTION

A number of symptoms result from stress encountered in daily life, including insomnia.

In order to deal with such stress, the sedative capacity of natural essential oils, such as lavender oil or camomile oil, has been used for a very long time.

However, these essential oils contain other compounds which have no sedative effect and are in general employed for their perfuming capacity.

The application of such oils is therefore limited by their perfuming capacity which may not be acceptable for stressed subjects, who do not like the perfume of these essential oils.

It has therefore appeared necessary to find sedative agents that may be used in all kinds of perfume compositions, without affecting the perfuming capacity of these compositions.

Synthetic chemical compounds as sedative agents for perfumes have been already proposed.

U.S. Pat. No. 5,141,921 describes perfume compositions containing 3-methyl-hexenoic acid and/or 7-octenoic acid.

These compositions give rise to psychological effects on users, such as stimulant and/or sedative effects.

U.S. Pat. No. 6,268,333 describes the use of 1,3-dimethoxy-5-methylbenzene as a sedative agent in perfumes.

JP Patent application 2000-86478 describes sedative aromatic compounds containing 0.5 to 50% by weight of a trialkoxybenzene represented by formula (I):

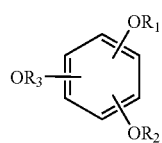

wherein $R_1$, $R_2$ and $R_3$, which may be the same or different, preferably same and each represents $CH_3$ or $C_2H_5$.

SUMMARY OF THE INVENTION

It has now been found, in a surprising way, that trimethoxybenzenes, which are compounds represented by the above formula (I), wherein $R_1$, $R_2$ and $R_3$, each represents a methyl group, give rise to a sedative effect when they are used in an amount of less than 0.5% by weight based on the total weight of the perfume composition.

The present invention therefore has as its objects
(1) a perfume composition, which comprises at least one trimethoxybenzene in an amount of less than 0.5% by weight based on the total weight of the perfume composition;
(2) the perfume composition according to 1 above, which comprises 0.01 to 0.4% by weight of the trimethoxybenzene, based on the total weight of the perfume composition;
(3) the perfume composition according to 1 or 2 above, wherein the trimethoxybenzene is 1,3,5-trimethoxybenzene;
(4) a method for providing sedation in a subject, which comprises applying a perfume composition comprising at least one trimethoxybenzene in an amount of less than 0.5% by weight based on the total weight of the perfume composition to the subject;
(5) the method according to 4 above, wherein the amount of the trimethoxybenzene is from 0.01 to 0.4% by weight based on the total weight of the perfume composition; and
(6) the method according to 4 or 5 above, wherein the trimethoxybenzene is 1,3,5-trimethoxybenzene.

DETAILED DESCRIPTION OF THE INVENTION

Figure 1:
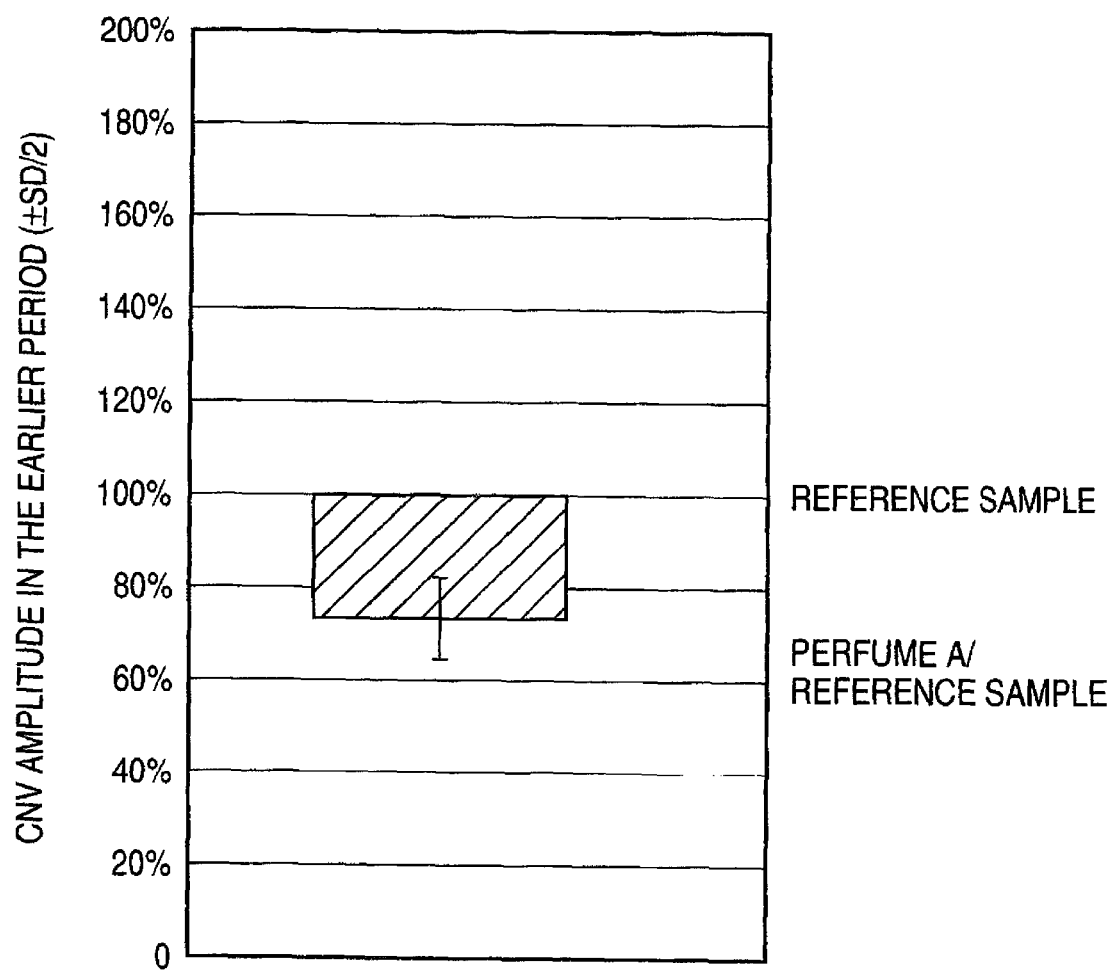
FIG. 1 is a graph showing CNV amplitude expressed with respect to a reference sample for perfume composition A.

According to the present invention, a trimethoxybenzene to be used is in an amount of less than 0.5% by weight, preferably 0.01 to 0.4% by weight based on the total weight of the perfume composition.

It is also possible according to the present invention to use a mixture of trimethoxybenzenes, provided that the total amount of trimethoxybenzenes is in an amount of less than 0.5% by weight, preferably 0.01 to 0.4% by weight, based on the total weight of the perfume composition.

In addition, among the trimethoxybenzenes to be used in the present invention, 1,3,5-trimethoxybenzene is preferable.

Trimethoxybenzenes can be obtained from commercial sources. They can easily be manufactured via the processes described or referred to by Wei et al, Organic Preparations and Procedures International Vol 35 (2003), 225, herein incorporated by reference.

The perfume compositions containing trimethoxybenzene according to the invention comprise at least one trimethoxybenzene and the other optional ingredient. Specifically, as the example of the perfume composition, there can be mentioned a perfume composition which comprises a trimethoxybenzene and a carrier which is acceptable for the perfume composition.

As the examples of the carrier which is acceptable for the perfume composition, solvents which can dissolve the trimethoxybenzene, such as ethanol, isopropanol, ethylene glycol, propylene glycol, butylene glycol, pentylene glycol, hexylene glycol, dipropylene glycol and the like, can be mentioned.

In the present invention, the expression "sedative effect" or "sedation" refers to the psychological aspects of well-being and includes effects of calming, soothing, relaxing, de-stressing etc.

In addition, according to the present invention, subjects in which the sedation is provided are animals, preferably mammals, and more preferably human.

The sedative agent according to the present invention is particularly suitable for perfumes used in toiletries, such as shampoos, after-shampoos, soaps, bath products, deodorants, body creams, eau de toilette and hygiene and beauty products.

In order to obtain the sedative effect, the perfume composition according to the present invention is preferably in an amount of from 0.001% to 1% by weight based on the total weight of the products, for example toiletries, such as shampoos, after-shampoos, soaps, bath products, deodorants, body creams, eau de toilette and hygiene and beauty products.

The sedative effect of trimethoxybenzene is determined by measuring the variations of negative electrical potential, called "contingent negative variations". (CNV) according to the method of Torii [Proceedings of the 19$^{th}$ Japanese Symposium on Taste and Smell, 65 (1985)], which is also described in detail in U.S. Pat. No. 6,268,333.

The contingent negative variations are small variations in cerebral potential related to psychological processes, such as attention, waiting, anticipation etc. as well as being related to changes in the state of consciousness.

According to this method, a luminous signal is emitted approximately 2 seconds after the audible signal, and the subject must switch off the luminous signal by pressing on the button as soon as the luminous signal is recognised.

When carrying out these experiments, a sample to be tested (perfume composition) or a reference sample (with no smell) is placed around 10 centimeters from the nose of the subject taking part in these experiments in such a way as to ensure that the compound is recognised at all times via the said subject's respiration.

An electrode for measuring the contingent negative variations is placed on the subject's forehead (the reference electrode is placed on the ear lobe).

The contingent negative variations measured during an early period of time going from 400 msec to 1000 msec after the audible signal and the amplitude of these variations is expressed with respect to a reference sample to which a value of 100% is given.

A sample tested whose amplitude is greater than 100% will be a stimulant product and a sample tested with an amplitude less than 100% will be a sedative.

The measurement of contingent negative variations has shown that trimethoxybenzene, and in particular 1,3,5-trimethoxybenzene, has a sedative effect when it is used in perfume compositions in an amount of less than 0.5% by weight, preferably from 0.01% to 0.4% by weight based on the total weight of the perfume composition.

The invention will now be described in more detail by the following illustrative and non-limiting examples:

EXAMPLE 1

Perfume Compositions

A perfume composition was prepared having a fruity and floral note of rose, by mixing the following components:

| Ingredients | CAS N° | % by weight |
|---|---|---|
| Hedione | 24851-98-7 | 25 |
| Galaxolide ® BB | 1222-05-5 | 15 |
| Lilial ® | 80-54-6 | 10 |
| Phenyl ethyl alcohol | 60-12-8 | 10 |
| Ethyl Linalool | 10339-55-6 | 5 |
| Iso E Super ® | 54464-57-2 | 5 |
| Cyclohexyl ethyl acetate | 21722-83-8 | 5 |
| Heliobouquet | 1205-17-0 | 2.5 |
| Linalyl acetate | 115-97-7 | 2.5 |

-continued

| Ingredients | CAS N° | % by weight |
|---|---|---|
| Habanolide ® | 34902-57-3 | 2.5 |
| Santalex T ® | 68877-29-2 | 2.5 |
| cis 3-Hexenyl salicylate | 65405-77-8 | 2.5 |
| Rose absolute (10% in DPG) | 8007-01-0 | 2.5 |
| L-Citronellol | 7540-51-4 | 2.5 |
| Essence of rose | 8015-77-8 | 2 |
| Geraniol | 106-24-1 | 2 |
| Heliotropin | 120-57-0 | 1 |
| Raspberry Ketone (10% in DPG) | 5471-51-2 | 0.5 |
| L-oxide of rose (1% in DPG) | 16409-43-1 | 0.5 |
| Dipropylene glycol (DPG) | | qsp 100% |

One of the two following were then added, based on the total weight of the perfume composition:
0.4% by weight of 1,3,5-trimethoxybenzene to the above perfume composition, so as to obtain perfume composition A; or
1% by weight of 1,3,5-trimethoxybenzene to the above perfume composition, obtaining perfume composition B.

EXAMPLE 2

CNV Amplitude

Five Japanese women took part in the test to determine the contingent negative variations according to the previously described experimental method.

The amplitude of the contingent negative variations was determined for each woman taking part in the test during the early period going from 400 msec to 1000 msec after the audible signal.

Figure 2:
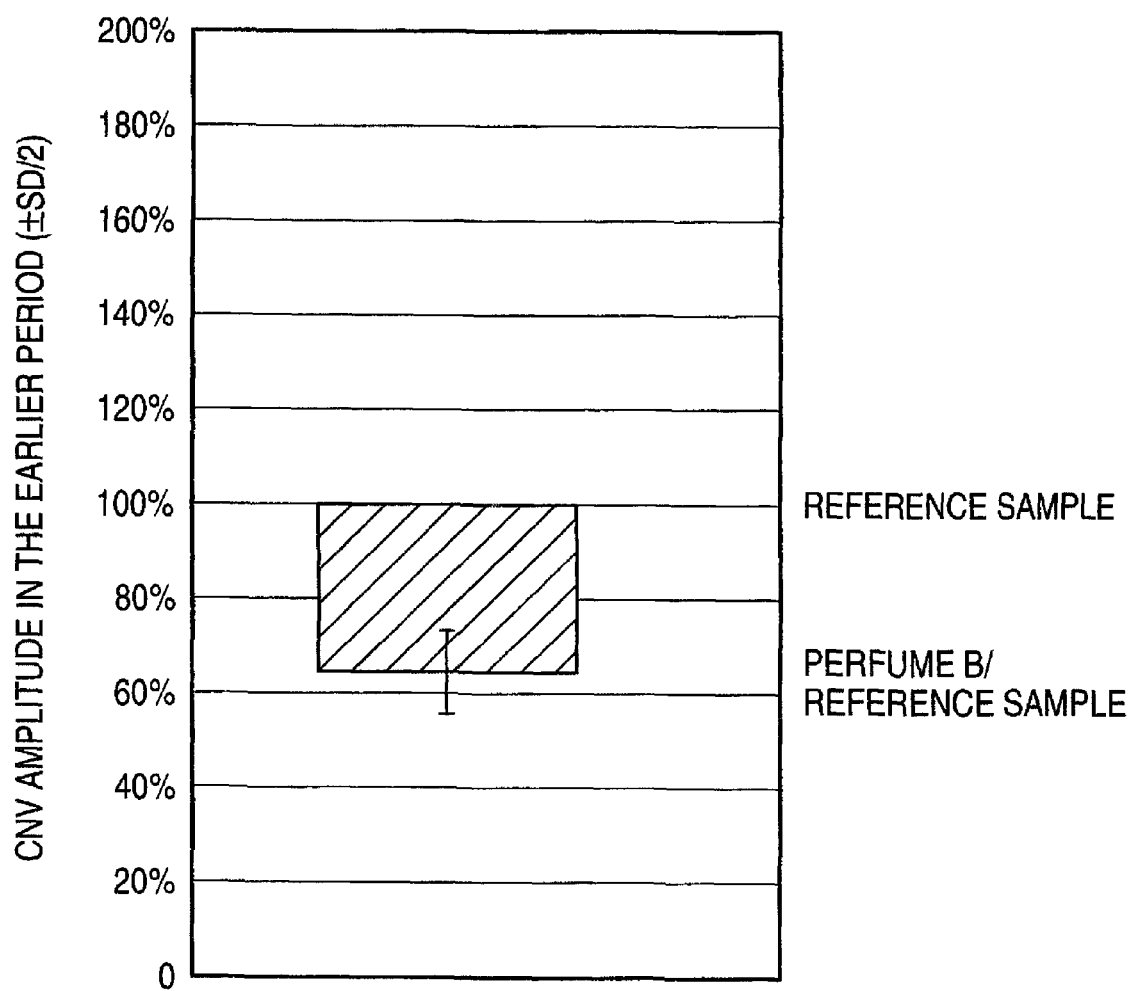
FIG. 2 is a graph showing CNV amplitude expressed with respect to a reference sample for perfume composition B.

FIGS. 1 and 2 represent graphically CNV amplitude expressed with respect to a reference sample for perfume composition A (FIG. 1) and for perfume composition B (FIG. 2).

It was observed, surprisingly, that the 1,3,5-trimethoxybenzene in an amount of 0.4% by weight (perfume composition A) also had a sedative effect like 1,3,5-trimethoxybenzene in an amount of 1% by weight (perfume composition B according to the prior art).

This application is based on French patent application No. 04/08726 filed on Aug. 6, 2004, the entire contents thereof being hereby incorporated by reference.

What is claimed is:

1. A method for providing sedation in a subject, which comprises applying a perfume composition to the subject in need of sedation, which perfume composition is contained in a product which is an after-shampoo, soap, bath product, deodorant, body cream, eau de toilette, hygiene product or beauty product, said perfume composition comprising at least one trimethoxybenzene which provides the sedation in the subject, wherein the amount of trimethoxybenzene is from 0.01 to less than 0.5% by weight based on the total weight of the perfume composition, wherein the product contains from $1 \times 10^{-7}$% to less than $5 \times 10^{-6}$% by weight of trimethoxybenzene based on the total weight of the product.

2. The method according to claim 1, wherein the amount of the trimethoxybenzene is from 0.01 to 0.4% by weight based on the total weight of the perfume composition.

3. The method according to claim 1, wherein the trimethoxybenzene is 1,3,5-trimethoxybenzene.

4. The method according to claim 2, wherein the trimethoxybenzene is 1,3,5-trimethoxybenzene.

5. The method according to claim 1, wherein the perfume composition is contained in the after-shampoo.

6. The method according to claim 1, wherein the perfume composition is contained in the soap.

7. The method according to claim 1, wherein the perfume composition is contained in the bath product.

8. The method according to claim 1, wherein the perfume composition is contained in the deodorant.

9. The method according to claim 1, wherein the perfume composition is contained in the body cream.

10. The method according to claim 1, wherein the perfume composition is contained in the eau de toilette.

11. The method according to claim 1, wherein the perfume composition is contained in the hygiene product.

12. The method according to claim 1, wherein the perfume composition is contained in the beauty product.

13. The method according to claim 1, wherein the product contains from $1 \times 10^{-7}\%$ to $4 \times 10^{-6}\%$ by weight of trimethoxybenzene based on the total weight of the product.

* * * * *